US011375883B2

(12) United States Patent
Takata (10) Patent No.: US 11,375,883 B2
(45) Date of Patent: Jul. 5, 2022

(54) LIGHT-SCANNING ENDOSCOPE, CORRECTING APPARATUS FOR LIGHT SCANNING ENDOSCOPE AND LIGHT-SCANNING-ENDOSCOPE OPERATING METHOD (71) Applicant: OLYMPUS CORPORATION, Tokyo (JP)

(72) Inventor: Yuhei Takata, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 901 days.

(21) Appl. No.: 16/010,608

(22) Filed: Jun. 18, 2018

(65) Prior Publication Data
US 2018/0303321 A1 Oct. 25, 2018

Related U.S. Application Data (63) Continuation of application No. PCT/JP2015/086293, filed on Dec. 25, 2015.

(51) Int. Cl.
A61B 1/00 (2006.01)
H01S 3/10 (2006.01)
G02B 26/12 (2006.01)
(Continued)

(52) U.S. Cl.
CPC ...... A61B 1/00172 (2013.01); A61B 1/00006 (2013.01); A61B 1/00009 (2013.01);
(Continued)

(58) Field of Classification Search
CPC ............ A61B 1/00172; A61B 1/00163; A61B 1/00165; A61B 1/0661; A61B 1/0669;
(Continued)

(56) References Cited

U.S. PATENT DOCUMENTS 6,845,190 B1* 1/2005 Smithwick ........... A61B 1/0008
385/1
2004/0212808 A1* 10/2004 Okawa ............... A61B 1/00172
356/479
(Continued)

FOREIGN PATENT DOCUMENTS

JP 5190267 B2 4/2013
JP 2015206981 A 11/2015
(Continued)

OTHER PUBLICATIONS

International Search Report dated Mar. 15, 2016 issued in PCT/JP2015/086293.

Primary Examiner — Ryan N Henderson
Assistant Examiner — Pamela F Wu
(74) Attorney, Agent, or Firm — Scully, Scott, Murphy & Presser, P.C.

(57) ABSTRACT

A light-scanning endoscope is provided with: a light-scanner that causes an optical fiber to be vibrated; a controller that causes light to be emitted from the optical fiber with the same phase as the vibrations; an adjusting unit that adjusts a distortion correction amount on the basis of a shape of a row of irradiation positions of the light on an imaging subject; and a phase correcting unit that corrects the phase in which the light is emitted on the basis of the adjusted distortion correction amount.

20 Claims, 6 Drawing Sheets (51) Int. Cl.
  *G02B 26/10* (2006.01)
  *H01S 3/101* (2006.01)
  *A61B 1/04* (2006.01)
  *A61B 1/06* (2006.01)
  *A61B 1/07* (2006.01)

(52) U.S. Cl.
  CPC .......... *A61B 1/00165* (2013.01); *A61B 1/042* (2013.01); *A61B 1/063* (2013.01); *A61B 1/0669* (2013.01); *A61B 1/07* (2013.01); *G02B 26/103* (2013.01); *G02B 26/127* (2013.01); *H01S 3/101* (2013.01); *H01S 3/10053* (2013.01)

(58) Field of Classification Search
  CPC ......... A61B 1/07; H01S 3/101; H01S 5/0071; H01S 5/02251; G05D 3/00
  USPC .............................. 250/227.26; 600/160, 182
  See application file for complete search history.

(56) References Cited

U.S. PATENT DOCUMENTS

| | | | |
|---|---|---|---|
| 2009/0316116 A1* | 12/2009 | Melville | A61B 1/07 353/31 |
| 2014/0332677 A1* | 11/2014 | Fujiwara | A61B 1/063 250/234 |
| 2015/0005579 A1* | 1/2015 | Yamabe | A61B 1/00057 600/109 |
| 2017/0041577 A1 | 2/2017 | Nishimura | |
| 2017/0090181 A1 | 3/2017 | Innami | |

FOREIGN PATENT DOCUMENTS

| | | |
|---|---|---|
| WO | 2006041452 A1 | 4/2006 |
| WO | 2015162860 A1 | 10/2015 |
| WO | 2015182137 A1 | 12/2015 |

* cited by examiner

LIGHT-SCANNING ENDOSCOPE, CORRECTING APPARATUS FOR LIGHT SCANNING ENDOSCOPE AND LIGHT-SCANNING-ENDOSCOPE OPERATING METHOD

CROSS-REFERENCE TO RELATED APPLICATIONS

This is a continuation of International Application PCT/JP2015/086293, with an international filing date of Dec. 25, 2015, which is hereby incorporated by reference herein in its entirety.

TECHNICAL FIELD

The present invention relates to a light-scanning endoscope and a light-scanning-endoscope operating method.

BACKGROUND ART

In the related art, there is a known light-scanning endoscope that scans laser light on an imaging subject along a spiral trajectory (for example, see PTL 1). It is known that distortion in the scanning direction occurs in a figure in an image acquired by means of a light-scanning endoscope due to displacements, in the scanning direction, of the actual irradiation positions of the laser light from ideal irradiation positions thereof. In PTL 1, the positions of laser-light spots on the imaging subject are detected by means of a PSD (Position Sensitive Detector), and figure distortion is corrected on the basis of the displacements of the detected spot positions from the ideal positions.

CITATION LIST

Patent Literature

{PTL 1} Publication of Japanese Patent No. 5190267

SUMMARY OF INVENTION

The present invention provides the following solutions.

A first aspect of the present invention is light-scanning endoscope including: a light-scanner that, by vibrating an optical fiber, scans light emitted from the optical fiber; a controller that controls a timing at which the light is emitted from the optical fiber so that the light is emitted with the same phase as the vibrations of the optical fiber; an adjusting unit that adjust a distortion correction amount on the basis of a shape of a row of irradiation positions, on an imaging subject, of the light emitted from the optical fiber; and a phase correcting unit that corrects the phase at which the light is emitted on the basis of the distortion correction amount adjusted by the adjusting unit.

A second aspect of the present invention is a light-scanning-endoscope operating method including: an emitting step of emitting, from a vibrating optical fiber, light with the same phase as the vibrations of the optical fiber; an adjusting step of adjusting a distortion correction amount on the basis of a shape of a row of irradiation positions of the light on an imaging subject; a correcting step of correcting, on the basis of the distortion correction amount adjusted in the adjusting step, the phase at which the light is emitted from the optical fiber; and a controlling step of controlling a timing at which the light is emitted from the optical fiber so that the light is emitted at the phase corrected in the correcting step.

DESCRIPTION OF EMBODIMENT

A light-scanning endoscope 1 according to an embodiment of the present invention will be described below with reference to the drawings.

Figure 1:
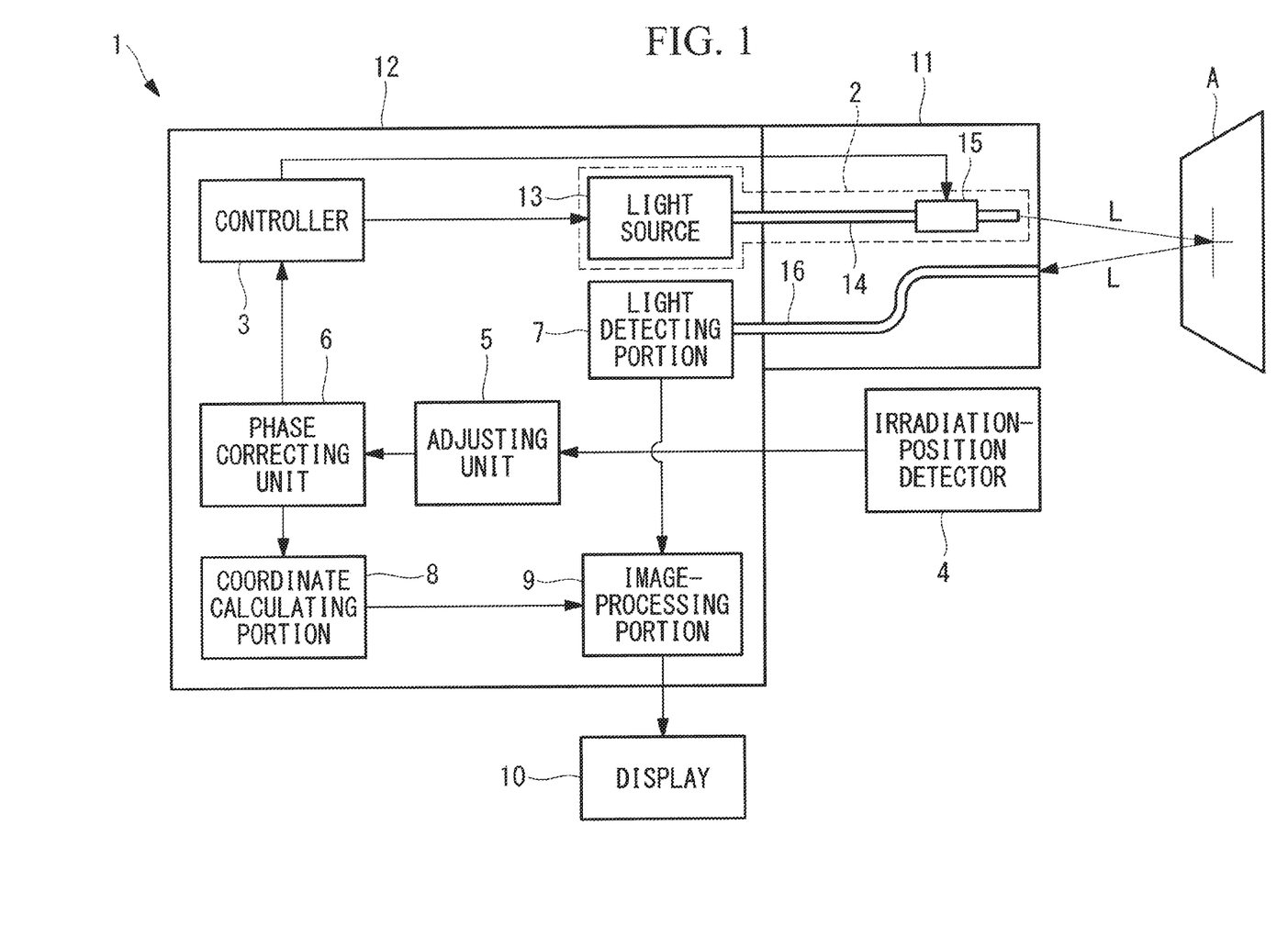
FIG. 1 is an overall configuration diagram of a light-scanning endoscope according to an embodiment of the present invention.

As shown in FIG. 1, the light-scanning endoscope 1 according to this embodiment is provided with: a light-scanner 2 that emits laser light L toward an imaging subject A while scanning the laser light L; a controller 3 that controls the light-scanner 2; an irradiation-position detector 4 that detects positions (irradiation positions) of spots of the laser light L on the imaging subject A; an adjusting unit 5 that adjusts a correction parameter (distortion correction amount) E for correcting figure distortion in an image; and a phase correcting unit 6 that corrects the emission timing of the laser light L on the basis of the correction parameter E.

Furthermore, the light-scanning endoscope 1 is provided with: a light detecting portion 7 that acquires detection values It by detecting observation light L' coming from the imaging subject A; a coordinate calculating portion 8 that calculates, on the basis of the correction parameter E, pixel coordinates (X, Y) to which the detection values It are assigned; an image-processing portion 9 that forms an image; and a display 10 that displays the image.

Reference sign 11 indicates a long, thin inserted portion that is inserted into a body, and reference sign 12 indicates a housing that is connected to a base end of the inserted portion 11.

The light-scanning endoscope 1 has a first mode for determining an optimal correction parameter E and a second mode for acquiring an image in which figure distortion is corrected on the basis of the correction parameter E; and is operated in one of the first mode and the second mode. In the first mode, the light-scanner 2, the controller 3, the irradiation-position detector 4, the adjusting unit 5, and the phase correcting unit 6 function. In the second mode, the light-scanner 2, the controller 3, the phase correcting unit 6, the light detecting portion 7, the coordinate calculating portion 8, and the image-processing portion 9 function.

The light-scanner 2 is provided with: a light source 13 that is provided in the housing 12 and outputs the laser light L; and an irradiation optical fiber 14 and an actuator 15 that are provided in the inserted portion 11.

The optical fiber 14 is disposed in the inserted portion 11 along a longitudinal direction thereof. The optical fiber 14 guides the laser light L supplied from the light source 13 and emits the laser light L from a distal end thereof.

The actuator 15 is, for example, a piezoelectric actuator provided with a piezoelectric element, and is attached to a distal-end portion of the optical fiber 14. The actuator 15 causes the distal end of the optical fiber 14 to be vibrated in radial directions of the optical fiber 14 in accordance with driving signals supplied from the controller 3.

The controller 3 supplies the actuator 15 with X-direction driving signals Dx(t) for causing the distal end of the optical fiber 14 to be vibrated in X-directions and Y-direction driving signals Dy(t) for causing the distal end of the optical fiber 14 to be vibrated in Y-directions. The X-directions and the Y-directions are radial directions of the optical fiber 14 and are directions that are orthogonal to each other. The driving signals Dx(t) and Dy(t) are represented as follows:

$$Dx(t)=M(t)\times\cos(2\pi ft), \text{ and}$$

$$Dy(t)=M(t)\times\sin(2\pi ft).$$

Figure 2:
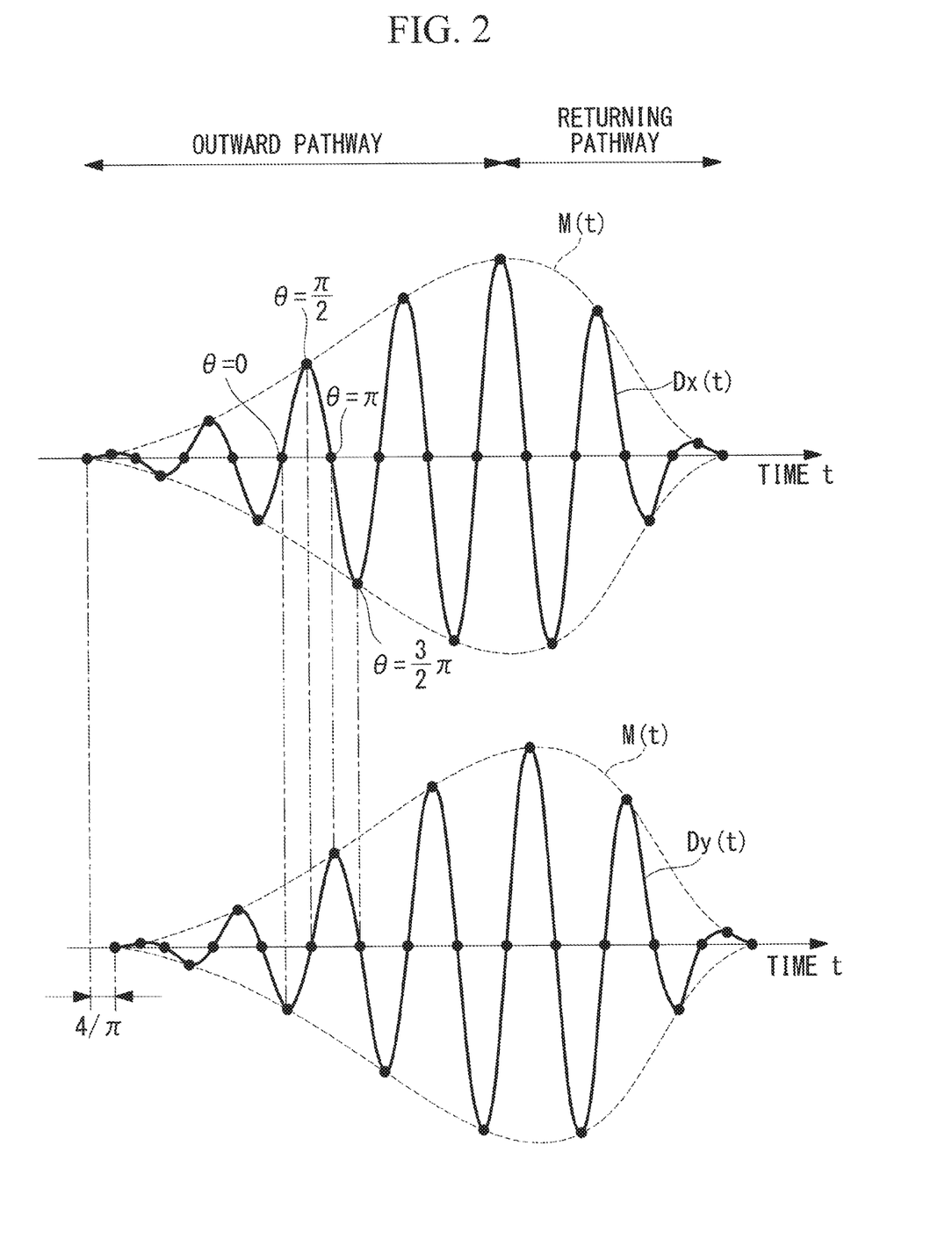
FIG. 2 is a diagram showing waveforms of an X-direction driving signal and a Y-direction driving signal that are supplied to an actuator in the light-scanning endoscope in FIG. 1.

FIG. 2 shows the driving signals Dx(t) and Dy(t). The amplitudes of the driving signals Dx(t) and the driving signals Dy(t) are modulated by substantially sinusoidal modulation signals M(t) represented by Expression (1) below. In Expression (1), $N_{OPEN}$ is a number of cycles in an outward pathway, and $N_{CLOSE}$ is a number of cycles in a returning pathway. Furthermore, phases of the driving signals Dx(t) and the driving signals Dy(t) are displaced from each other by an amount $\pi/4$. Note that the example described here is such that vibrations occur along a spiral trajectory that is projected, in the outward pathway, toward an outer circumference from a center, and that is projected, in the returning pathway, from the outer circumference toward the center.

{Eq. 1}

$$M(t) = \begin{cases} \frac{1}{2}\left\{1 - \cos\left(\frac{\pi ft}{N_{OPEN}}\right)\right\} \\ \quad \left(0 \le t \le \frac{N_{OPEN}}{f}\right) \\ \frac{1}{2}\left\{1 - \cos\left(\pi + \frac{\pi ft}{N_{CLOSE}} - \frac{\pi N_{OPEN}}{N_{CLOSE}}\right)\right\} \\ \quad \left(\frac{N_{OPEN}}{f} < t \le \frac{N_{OPEN}+N_{CLOSE}}{f}\right) \end{cases} \quad (1)$$

By simultaneously supplying the actuator 15 with such driving signals Dx(t) and Dy(t), the distal end of the optical fiber 14 is vibrated along a spiral trajectory substantially in a plane that is orthogonal to the longitudinal direction of the optical fiber 14. By doing so, the laser light L emitted from the distal end of the inserted portion 11 is scanned on the imaging subject A along a spiral scanning trajectory B.

Furthermore, the controller 3 controls the light source 13 by using methods that are different from each other in the first mode and the second mode.

In the second mode, the controller 3 controls the light source 13 so as to continuously output the laser light L.

In the first mode, first the controller 3 controls the light source 13 so as to emit the laser light L when the phase $\theta$(rad) of the driving signal Dx(t) is 0, $\pi/2$, $\pi$, and $3\pi/2$. Subsequently, upon receiving information about a corrected phase $\theta+\Delta\theta$ (described later) from the phase correcting unit 6, the controller 3 controls the light source 13 so as to emit the laser light L when the phase $\theta$ of the driving signal Dx(t) is $0+\Delta\theta$, $\pi/2+\Delta\theta$, $\pi+\Delta\theta$, and $3\pi/2+\Delta\theta$. The controller 3 ends the first mode when a signal indicating completion of the adjustment of the correction parameter E is received from the phase correcting unit 6.

Figure 3:
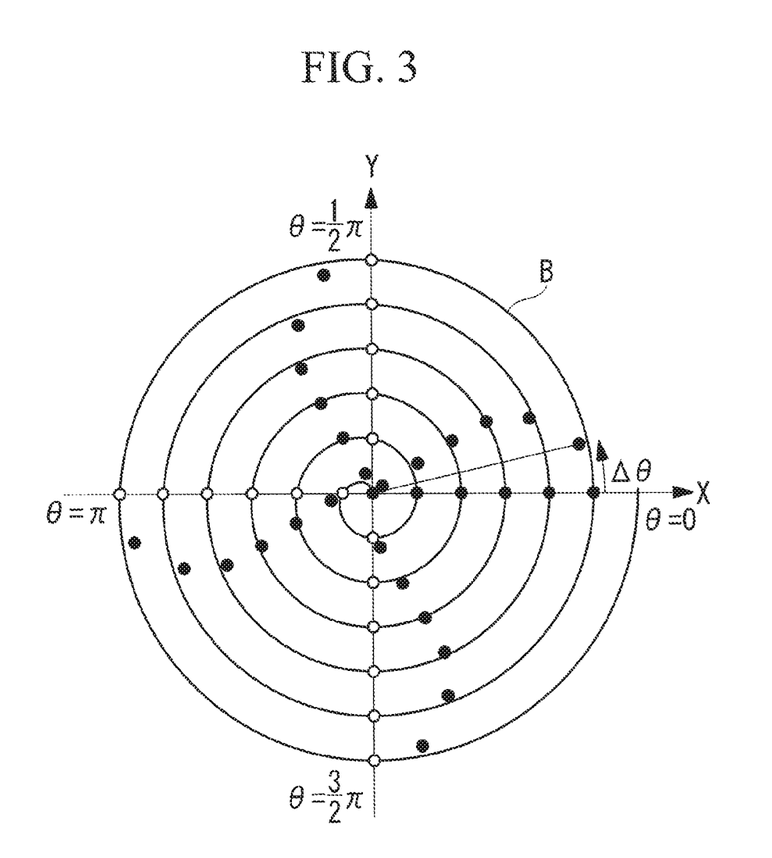
FIG. 3 is a diagram showing rows of spots of laser light formed on an imaging subject in a first mode.

The laser light L that is output in the same phase $\theta$ irradiates positions at the same rotational angles in the scanning trajectory B. Therefore, as shown in FIG. 3, spots of the laser light L in the same phase are ideally arrayed in a straight line on the imaging subject A. In FIG. 3, open circles indicate ideal spot positions that are theoretically calculated for the laser light L on the basis of the amplitudes of the driving signals Dx(t) and Dy(t).

However, the actual spot positions of the laser light L do not necessarily coincide with the ideal positions thereof, and there are cases in which an actual row of spots does not form a straight line. In FIG. 3, filled circles indicate the actual spot positions of the laser light L. The actual spot positions are displaced from the ideal positions in the scanning direction. Because the displacements of the spot positions do not occur when the driving signals Dx(t) and Dy(t) are not modulated (in other words, when the amplitudes of the driving signals Dx(t) and Dy(t) are constant), it is considered that the displacements are caused by modulating the driving signals Dx(t) and Dy(t) (in other words, changes over time in the amplitudes of the vibrations of the distal end of the optical fiber 14).

Because the changes over time in the amplitudes of the driving signals Dx(t) and Dy(t) differ depending on the number of cycles N (the order of the circles from the center when the scanning trajectory B is considered to be a collection of concentric circles) in the scanning trajectory B, the amounts by which the spot positions of the laser light L are displaced from the ideal positions thereof (rotational angles about the center of the scanning trajectory B) also differ depending on the number of cycles N, as shown in FIG. 3. As a result, shapes of the rows of the spots are distorted.

The irradiation-position detector 4 two-dimensionally detects the spot positions of the laser light L on the imaging subject A. As such an irradiation-position detector 4, for example, a two-dimensional light detecting apparatus, such as a CCD camera, a PSD, or the like, is employed, and a two-dimensional image of the rows of spots on a screen is acquired by the irradiation-position detector 4. Information about the spot positions of the laser light L detected by the irradiation-position detector 4 is transmitted to the adjusting unit 5.

The adjusting unit 5 adjusts the correction parameter E in Expression (2) below and transmits the adjusted correction parameter E to the phase correcting unit 6. In Expression (2), $\Delta\theta(t)$ is the phase angle, and f is the frequency (drive frequency) of the driving signals.

{Eq. 2}

$$\Delta\theta(t) = \begin{cases} E \cdot \dfrac{\sin\left(\dfrac{\pi ft}{N_{OPEN}}\right)}{\dfrac{1}{2}\left\{1 - \cos\left(\dfrac{\pi ft}{N_{OPEN}}\right)\right\}} \\ \quad \left(0 \le t \le \dfrac{N_{OPEN}}{f}\right) \\ E \cdot \dfrac{\sin\left(\pi + \dfrac{\pi ft}{N_{CLOSE}} - \dfrac{\pi N_{OPEN}}{N_{CLOSE}}\right)}{\dfrac{1}{2}\left\{1 - \cos\left(\pi + \dfrac{\pi ft}{N_{CLOSE}} - \dfrac{\pi N_{OPEN}}{N_{CLOSE}}\right)\right\}} \\ \quad \left(\dfrac{N_{OPEN}}{f} < t \le \dfrac{N_{OPEN}+N_{CLOSE}}{f}\right) \end{cases} \quad (2)$$

As shown in FIG. 3, the phase angle Δθ(t) is a center angle of an arc extending from an ideal spot position to an actual spot position. The numerator on the right side of Expression (2) represents a change over time in the modulation signal M(t) (a time derivative of the modulation signal M(t)), in other words, a change over time in the amplitude of the vibrations of the distal end of the optical fiber 14. The phase angle Δθ(t) is a function of the number of cycles N and the change over time in the amplitude of the vibrations of the distal end of the optical fiber 14, and the correction parameter E is a coefficient in the function.

Here, upon receiving the information about the spot positions of the laser light L from the irradiation-position detector 4, the adjusting unit 5 first calculates an index value that represents the linearity of a row of spots and assesses the linearity of the row of spots on the basis of the index value. In the case in which the index value is equal to or greater than a predetermined threshold ε, the adjusting unit 5 adjusts the correction parameter E. On the other hand, in the case in which the index value is less than the predetermined threshold ε, the adjusting unit 5 does not execute further adjustment of the correction parameter E and transmits signals indicating the completion of the correction-parameter-E adjustment to the phase correcting unit 6 and the controller 3.

Figure 4:
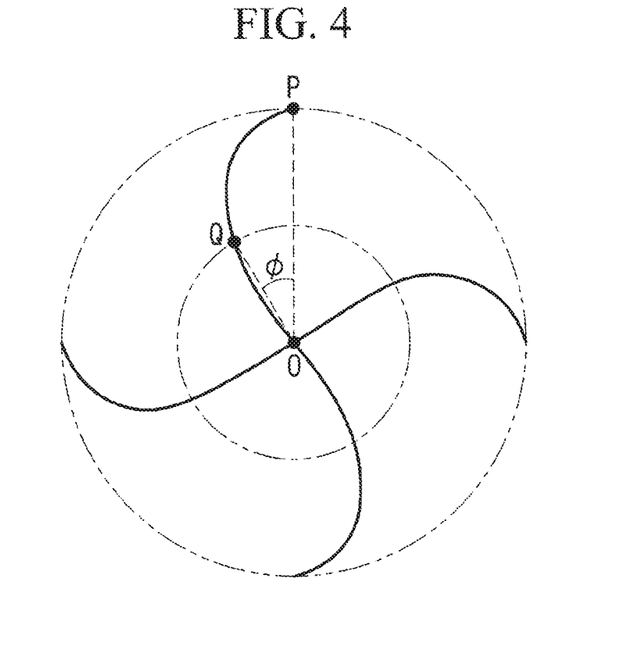
FIG. 4 is a diagram for explaining an example of an index value representing the linearity of a row of spots.

As shown in FIG. 4, for example, an angle φ of the angle POQ is used as the index value, and the shape of a row of spots is determined to be a straight line when φ<ε. In FIG. 4, a point O is an intersection of two lines when lines are drawn by connecting spots in the same rows (spots of the laser light L emitted in the same phases θ), a point P indicates a spot position at the outermost circumference on the scanning trajectory B, and a point Q is an intersection of one of the lines and a circle having a radius that is half the radius of a circle on the outermost circumference. In this case, the threshold ε is set to be an angle corresponding to 1 pixel in an image.

Figure 5:
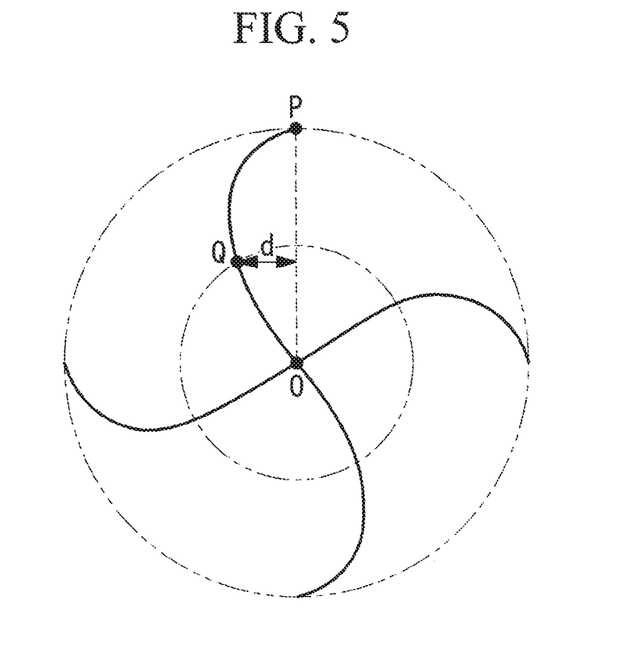
FIG. 5 is a diagram for explaining another example of the index value representing the linearity of a row of spots.

Alternatively, as shown in FIG. 5, a distance d between a straight line OP and the point Q is used as the index value, and the shape of a row of spots is determined to be a straight line when d<ε. In this case, the threshold ε is set to be a distance that corresponds to 1 pixel in an image.

In the first mode, the phase correcting unit 6 calculates a phase angle Δθ (correction amount) for each number of cycles N by substituting the correction parameter E received from the adjusting unit 5 into Expression (2), calculates a corrected phase θ+Δθ by shifting the phase θ in which the laser light L is output by an amount corresponding to the phase angle Δθ, and transmits information about the corrected phase θ+Δθ to the controller 3. By doing so, the phase θ of the laser light L to be output next is shifted by an amount corresponding to Δθ in accordance with the correction parameter E, and thus, the actual spot positions are brought closer to the ideal positions by an amount corresponding to Δθ. Upon receiving the signals indicating the completion of the adjustment of the correction parameter E from the adjusting unit 5, the phase correcting unit 6 retains the information about the correction parameter E that is finally received from the adjusting unit 5.

In the second mode, the phase correcting unit 6 calculates, on the basis of the waveforms of the driving signals Dx(t) and Dy(t), a phase θt of the vibrations of the distal end of the optical fiber 14 at a time t at which the observation light L' is detected by the light detecting portion 7. In addition, the phase correcting unit 6 calculates, on the basis of Expression (2), a phase angle Δθt by using the calculated phase θt and the correction parameter E that is finally retained in the first mode. The phase correcting unit 6 transmits information about the phase angle Δθt to the coordinate calculating portion 8.

Note that, instead of computing the phase angle Δθ on the basis of Expression (2), the phase correcting unit 6 may store a table in which the correction parameters E are associated with phase angles Δθ that are calculated in advance on the basis of Expression (2), and may read out, from the table, a phase angle Δθ that corresponds to a correction parameter E received from the adjusting unit 5.

The light detecting portion 7 is connected to a base end of the receiving optical fiber 16 that is disposed in the inserted portion 11. The distal end of the optical fiber 16 is disposed on a distal-end surface of the inserted portion 11. The observation light L' (for example, reflected light of the laser light L or fluorescence excited by the laser light L) generated at the imaging subject A by irradiation by the laser light L is received at the distal-end surface of the optical fiber 16 and is guided to the light detecting portion 7 by the optical fiber 16. Although FIG. 1 shows only one optical fiber 16, a plurality of optical fibers 16 may be provided in the inserted portion 11. The light detecting portion 7 detects, at certain time intervals, the observation light L' received via the optical fiber 16, and transmits the detection values It that indicate the intensity of the detected observation light L' to the image-processing portion 9.

The coordinate calculating portion 8 computes coordinates (x, y) of irradiation positions of the laser light L at the detection time t in the scanning trajectory B on the basis of the detection time t, the phase angle Δθt, and the amplitudes of the driving signals Dx(t) and Dy(t). Here, the coordinate calculating portion 8 calculates coordinates (x, y)=(Dx(θ+Δθ), Dy(θ+Δθ)) on the basis of the amplitudes of the driving signals Dx(t) and Dy(t) in the phase θt+Δθt that is shifted from the phase θt by an amount corresponding to the phase angle Δθt, instead of the phases θt of the driving signals Dx(t) and Dy(t) at the detection time t. Subsequently, the coordinate calculating portion 8 calculates pixel coordinates (X, Y) on the basis of the irradiation-position coordinates (x, y) and outputs the calculated pixel coordinates (X, Y) to the image-processing portion 9.

The image-processing portion 9 forms an image by assigning, to pixels at the coordinates (X, Y) received from the coordinate calculating portion 8, the detection values It of the observation light L' detected at corresponding detection times t. The formed image is transmitted to the display 10, and is displayed on the display 10.

Next, the operation of the thus-configured light-scanning endoscope 1 will be described.

In order to acquire an image of an imaging subject A by using the light-scanning endoscope 1 according to this embodiment, first, the optimal correction parameter E is obtained by operating the light-scanning endoscope 1 in the first mode.

Specifically, a user prepares a flat screen as the imaging subject A, and disposes the screen facing the distal end of the inserted portion 11 so as to be orthogonal to the longitudinal direction of the inserted portion 11. Next, the user operates the light-scanning endoscope 1 in the first mode.

Figure 6:
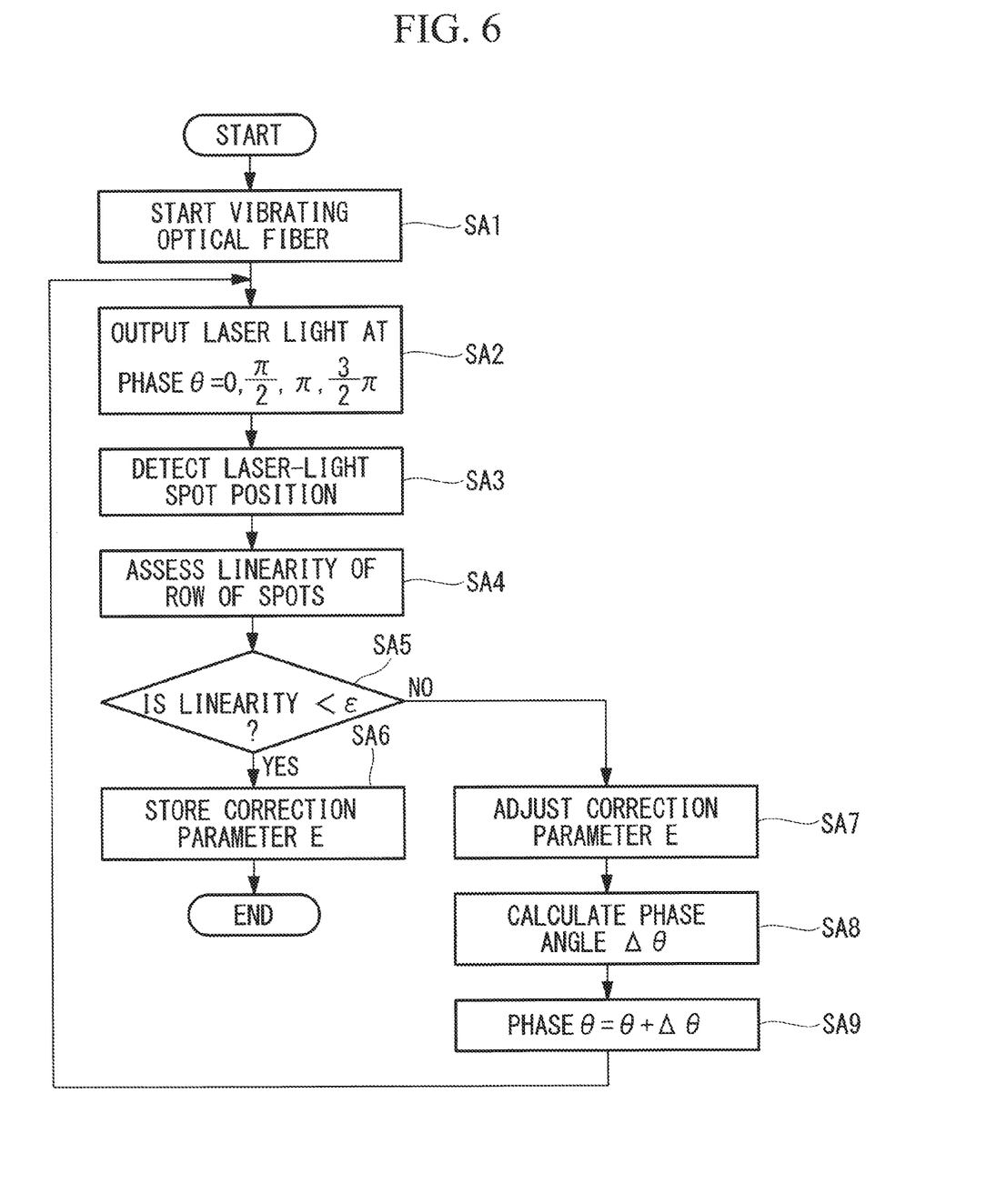
FIG. 6 is a flowchart showing the operation in the first mode of the light-scanning endoscope in FIG. 1.

When the operation in the first mode is started, as shown in FIG. 6, the driving signals Dx(t) and Dy(t) start to be supplied to the actuator 15 from the controller 3, thus causing the distal end of the optical fiber 14 to be vibrated (step SA1), and the laser light L is output from the light source 13 only when the phase of the driving signal Dx(t) is 0, π/2, π, and 3π/2 (emitting step SA2). By doing so, the laser light L is intermittently radiated on the screen along the spiral scanning trajectory B, and thus, rows of spots arrayed in two-axial directions orthogonal to each other appear on the screen. The spot positions on the screen are detected by the irradiation-position detector 4 (irradiation position detecting-step SA3), and the spot-position information is transmitted to the adjusting unit 5.

In the adjusting unit 5, the index values that represent the linearities of the rows of spots are calculated on the basis of the spot positions (step SA4). In the case in which the index values are less than the predetermined threshold E ("YES" in step SA5), the current correction parameter E is retained by the phase correcting unit 6 (step SA6), and the first mode is ended.

On the other hand, in the case in which the index values are equal to or greater than the predetermined threshold ε ("NO" in step SA5), the correction parameter E is subsequently adjusted in the adjusting unit 5 (adjusting step SA7). Next, in the phase correcting unit 6, the phase angle Δθ for each number of cycles N is calculated on the basis of Expression (2) by using the adjusted correction parameter E (step SA8), and the corrected phase θ+Δθ, which has been corrected by an amount corresponding to the phase angle Δθ, is calculated (correcting step SA9).

Next, the controller 3 controls the light source 13 so as to output the laser light L only when the phase of the driving signal Dx(t) is 0+Δθ, π/2+Δθ, π+Δθ, and 3π/2+Δθ (controlling step SA2). By doing so, the spot positions of the laser light L are moved about the center of the scanning trajectory B by an amount corresponding to the phase angle Δθ in which the magnitude thereof is in accordance with the correction parameter E.

As has been described above, by moving the individual spot positions of the laser light L by amounts corresponding to the phase angle Δθ calculated for each number of cycles N, the linearities of the rows of the spots are improved. Therefore, the index values calculated in the subsequent step SA4 take smaller values. Steps SA2 to SA5 and SA7 to SA9 are repeated until the index values become less than the predetermined threshold e.

Figure 7:
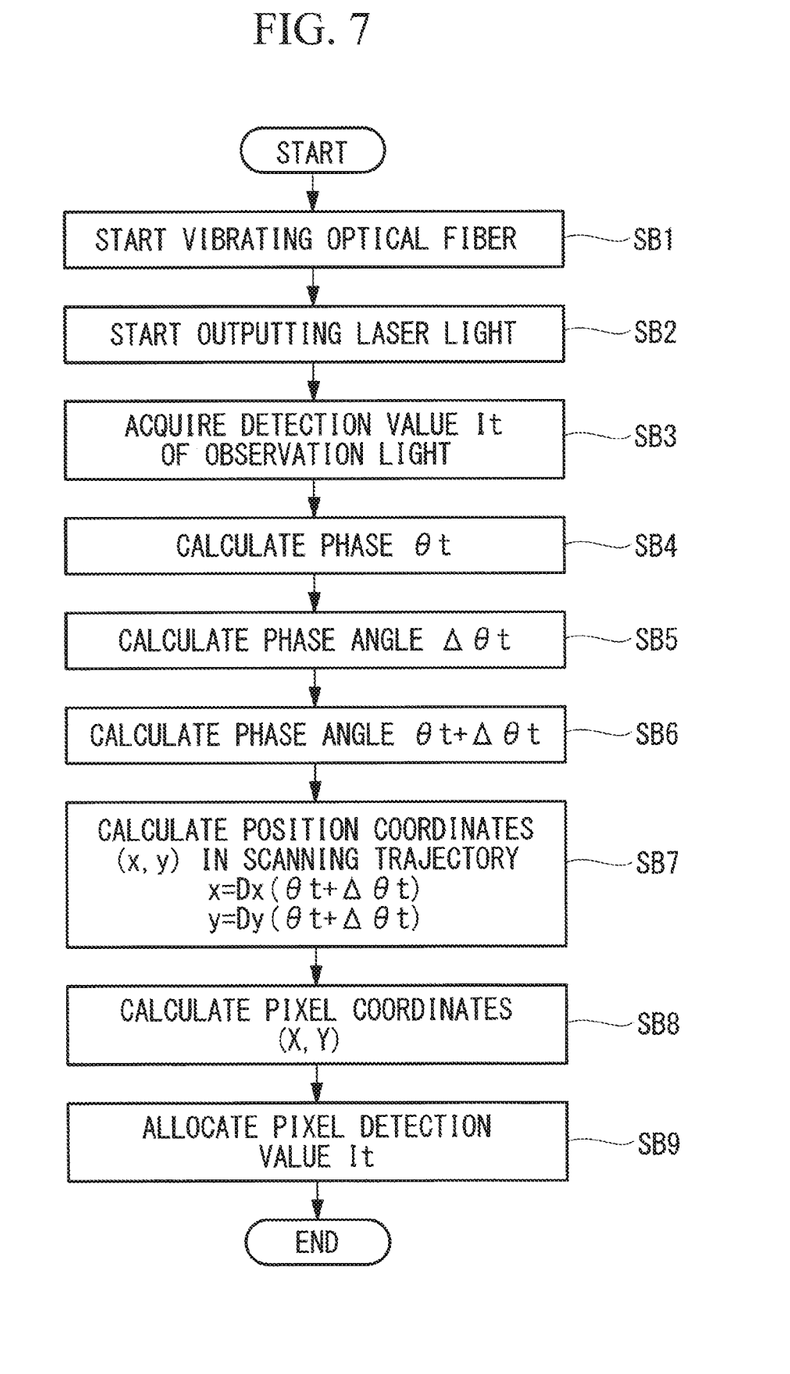
FIG. 7 is a flowchart showing the operation in a second mode of the light-scanning endoscope in FIG. 1.

After ending the first mode, the user inserts the inserted portion 11 into a body, and observes the body interior by operating the light-scanning endoscope 1 in the second mode.

When the operation in the second mode is started, as shown in FIG. 7, the driving signals start to be supplied to the actuator 15 from the controller 3 (step SB1), and the laser light L is continuously output from the light source 13 (step SB2). By doing so, the laser light L is continuously radiated onto a surface of the imaging subject A along the spiral scanning trajectory B, and the observation light L' is generated at the irradiation positions of the laser light L. The observation light L' is received by the optical fiber 16 and is detected by the light detecting portion 7 (step SB3), and the detection values It of the observation light L' are transmitted to the image-processing portion 9.

Next, in the phase correcting unit 6, the phase θt of the driving signals at a time t when the detection values It are detected is calculated (step SB4), and the phase angle Δθt is calculated on the basis of Expression (2) by using the phase θt and the optimal correction parameter E retained in step SA6 (step SB5).

Next, in the coordinate calculating portion 8, the amplitudes (Dx(θ+Δθ), Dy(θ+Δθ)) of the driving signals Dx(t) and Dy(t) at the corrected phase θt+Δθt, which is shifted from the phase θt by an amount corresponding to the phase angle Δθt (step SB6), are calculated in the form of the coordinates (x, y) of the irradiation positions of the laser light L at the detection time t (step SB7), and the pixel coordinates (X, Y) are calculated on the basis of the coordinates (x, y) (step SB8).

Next, in the image-processing portion 9, an image is formed (step SB9) by assigning the detection values It to the pixels at the coordinates (X, Y) (step SB9).

As has been described above, with this embodiment, by outputting the laser light L in the same phase, rows of spots of the laser light L are formed on the screen, and the correction parameter E to be used to correct image distortion is determined on the basis of the linearities of the rows of spots. In this way, by determining the correction parameter E on the basis of the shape of arrays of a plurality of spots instead of the individual spot positions, it is possible to determine a correction parameter E in which the influence of optical artifacts is removed. Also, by calculating the phase angle Δθ for correcting distortion by using the optimized correction parameter E, it is possible to form an image in which figure distortion in the scanning direction of the laser light L is eliminated.

Furthermore, by using the phase angles Δθ that are proportional to the changes over time in the amplitudes of the vibrations of the distal end of the optical fiber 14 at the individual numbers of cycles N, there is an advantage in that it is possible to accurately correct the displacements of the irradiation positions of the laser light L, which differ for each number of cycles N, and thus, it is possible to accurately correct figure distortion.

In this embodiment, the screen may be disposed at a position that is farther away from the distal end of the inserted portion 11 so that figures of the rows of spots on the screen are enlarged.

By doing so, it is possible to enhance the precision of assessing the linearities of the rows of spots, and thus, it is possible to enhance the precision of correcting image distortion.

In this embodiment, the timing at which the laser light L is output from the light source 13 may be changed so long as it is possible to assess the linearities of the rows of spots. For example, the laser light L may be emitted only when the phase θ=0. Alternatively, the interval of the phase θ may be set at a phase other than π/2, for example, π/6. It is preferable that the intervals of the phase θ in which the laser light L is output be equal intervals.

In the case in which the interval of the phase θ in which the laser light L is output is increased, because the number of rows of spots to be assessed is decreased, it is possible to reduce the amount of work. On the other hand, in the case in which the interval of the phase θ in which the laser light L is output is decreased, it is possible to assess partial deviation of a lens or the like.

In this embodiment, although Expression (2) is used as a function that represents the relationship between the number of cycles N and the phase angle Δθ, alternatively, a polynomial expression may be used. As a polynomial expression, for example, it is possible to use Expression (3) below. Expression (3) is an expression in which a Taylor expansion is performed on sin α/(1−cos α) at α=π assuming that 2πft/N=α. By using a polynomial expression, it is possible to reduce the amount of internal memory.

$$\Delta\theta = E\{\pi/2 - \alpha/2 + (\pi-\alpha)^3/24 + (\pi-\alpha)^5/240 + 17(\pi-\alpha)^7/40320 + 31(\pi-\alpha)^9/725760 + \ldots + 221930581(\pi-\alpha)^{19}/486580401635328000\} \quad (3)$$

Furthermore, by preparing a plurality of polynomial expressions, the polynomial expressions may be separately used in accordance with the number of cycles N. The optimal function Δθ(t) differs between when the number of cycles N is low and when the number of cycles N is high. Therefore, by separately using the polynomial expressions in accordance with the number of cycles N, it is possible to more accurately calculate the phase angle Δθ.

In this embodiment, although the laser light L is scanned in a spiraling manner, alternatively, Lissajous scanning may be employed.

In Lissajous scanning also, as with the case of spiral scanning, a distortion associated with modulation of the amplitudes of the driving signals occurs. Therefore, it is possible to correct the distortion by using the above-described method.

In this embodiment, although the adjusting unit 5 automatically adjusts the correction parameter E on the basis of the shapes of the rows of spots acquired by the irradiation-position detector 4, alternatively, the user may manually adjust the correction parameter E.

In this case, the adjusting unit 5 is configured so that the user can input the value of the correction parameter E. For example, the adjusting unit 5 may be a graphical user interface that displays, on the display 10, a graphic for inputting the value of the correction parameter E by using a keyboard. Alternatively, the adjusting unit 5 may be a dial with which it is possible to set the correction parameter E in accordance with the rotational angle thereof.

In this embodiment, as the drive frequency f, a frequency that is equal to the resonance frequency of the irradiation optical fiber 14 or a frequency in the vicinity of the resonance frequency is used. The manner in which image distortion occurs changes in accordance with the magnitude relationship between the resonance frequency of the optical fiber 14 and the drive frequency f, as described below.

In the case in which the drive frequency f is lower than the resonance frequency, the phase of the driving signals and the phase of the vibrations of the optical fiber 14 become identical when the optical fiber 14 is vibrated at a certain amplitude. When the amplitude of the vibrations of the optical fiber 14 is modulated, in the outward pathway, the phase of the vibrations of the optical fiber 14 is delayed with respect to the phase of the driving signals, and, in the returning pathway, the phase of the vibrations of the optical fiber 14 is advanced with respect to the phase of the driving signals. As the drive frequency f approaches the resonance frequency, the delay and the advance of the phase are increased.

In the case in which the drive frequency f is greater than the resonance frequency, the phase of the vibrations of the optical fiber 14 is delayed by an amount $\pi$ with respect to the phase of the driving signals when the optical fiber 14 is vibrated at a certain amplitude. When the amplitude of the vibrations of the optical fiber 14 is modulated, in the outward pathway, the phase of the vibrations of the optical fiber 14 is advanced with respect to the phase of the driving signals, and, in the returning pathway, the phase of the vibrations of the optical fiber 14 is delayed with respect to the phase of the driving signals. As the drive frequency f approaches the resonance frequency, the delay and the advance of the phase are increased.

In the case in which the drive frequency f is equal to the resonance frequency, the phase of the vibrations of the optical fiber 14 is delayed by an amount $\pi/2$ with respect to the phase of the driving signals when the optical fiber 14 is vibrated at a certain amplitude. When the amplitude of the vibrations of the optical fiber 14 is modulated, the phase of the vibrations of the optical fiber 14 tends to greatly fluctuate with respect to the phase of the driving signals.

From the above-described embodiments and modifications thereof, the following aspects of the invention are derived.

A first aspect of the present invention is light-scanning endoscope including: a light-scanner that, by vibrating an optical fiber, scans light emitted from the optical fiber; a controller that controls a timing at which the light is emitted from the optical fiber so that the light is emitted with the same phase as the vibrations of the optical fiber; an adjusting unit that adjust a distortion correction amount on the basis of a shape of a row of irradiation positions, on an imaging subject, of the light emitted from the optical fiber; and a phase correcting unit that corrects the phase at which the light is emitted on the basis of the distortion correction amount adjusted by the adjusting unit.

With the present invention, by causing the light to be emitted from the vibrating optical fiber in the same phase by means of the light-scanner, the light irradiation positions on the imaging subject are arrayed in a single row. Also, by detecting the irradiation positions by means of the irradiation-position detector, the shape of the row of the irradiation positions is acquired. Although the row of the irradiation positions becomes a straight line when the light irradiates ideal irradiation positions, the shape of the row of the irradiation positions is distorted when the actual irradiation positions of the light are displaced from the ideal irradiation positions in a light-scanning direction.

The phase correcting unit shifts the phase in which the light is emitted by an amount based on the distortion correction amount adjusted by the adjusting unit. By doing so, the light irradiation positions are moved in the scanning direction and are brought closer to the ideal irradiation positions, and thus, the linearity of the row of the irradiation positions is improved.

As has been described above, the distortion correction amount that is adjusted on the basis of the shape of the row of the plurality of irradiation positions instead of individual irradiation positions is less likely to be affected by an optical artifact. Therefore, by using such a distortion correction amount to correct a figure distortion in an image, it is possible to correct the figure distortion without being affected by an optical artifact.

The above-described first aspect may be provided with an irradiation-position detector that detects the light irradiation positions on the imaging subject.

In the above-described first aspect, the irradiation-position detector may be provided with a two-dimensional light detecting apparatus that detects the irradiation positions that are two-dimensionally arranged on the imaging subject.

By doing so, it is possible to detect the shape of the row of the light irradiation positions by means of a simple configuration.

In the above-described first aspect, the controller may control the timing at which the light is emitted from the optical fiber so that the light is emitted at an equal phase interval.

By doing so, it is possible to form a row of spots that are arrayed on the imaging subject at equal angles.

In the above-described first aspect, the light-scanner may cause an amplitude of the vibrations of the optical fiber to change over time, and the phase correcting unit may calculate a correction amount for the phase on the basis of the change over time in the amplitude of the vibrations of the optical fiber in addition to the distortion correction amount.

The amounts by which the actual irradiation positions of the light are displaced from the ideal irradiation positions are correlated with the change over time in the amplitude of the vibrations of the optical fiber. Therefore, by using the phase correction amount calculated on the basis of the change over time in the amplitude of the vibrations, it is possible to more precisely correct the displacements in the irradiation positions.

A second aspect of the present invention is a light-scanning-endoscope operating method including: an emitting step of emitting, from a vibrating optical fiber, light with the same phase as the vibrations of the optical fiber; an adjusting step of adjusting a distortion correction amount on the basis of a shape of a row of irradiation positions of the light on an imaging subject; a correcting step of correcting, on the basis of the distortion correction amount adjusted in the adjusting step, the phase at which the light is emitted from the optical fiber; and a controlling step of controlling a timing at which the light is emitted from the optical fiber so that the light is emitted at the phase corrected in the correcting step.

The present invention affords an advantage in that it is possible to accurately correct figure distortion in the light-scanning direction without being affected by optical artifacts.

REFERENCE SIGNS LIST 1 light-scanning endoscope
2 light-scanner
3 controller
4 irradiation-position detector
5 adjusting unit
6 phase correcting unit
7 light detecting portion
8 coordinate calculating portion
9 image-processing portion
10 display
11 inserted portion
12 housing
13 light source
14, 16 optical fiber
15 actuator
A imaging subject
B scanning trajectory

The invention claimed is:

1. A light-scanning endoscope comprising:
a light-scanner that, by vibrating an optical fiber, scans light emitted from the optical fiber; and
one or more processors comprising hardware, the one or more processors being configured to:
control a timing at which the light is emitted from the optical fiber so that the light is emitted with the same phase as the vibrations of the optical fiber;
evaluate a linearity of a row of light irradiation positions, on an imaging subject, of the light emitted from the optical fiber;
based on a result of the evaluation, adjust a distortion correction amount to bring the row closer to a straight line; and
based on the adjusted distortion correction amount, correct the phase at which the light is emitted.

2. The light-scanning endoscope according to claim 1, further comprising a camera configured to detect the light irradiation positions on the imaging subject.

3. The light-scanning endoscope according to claim 2, wherein the controlling of the timing controls the timing at which the light is emitted from the optical fiber so that the light is emitted at equal phase intervals.

4. The light-scanning endoscope according to claim 3, wherein
the light-scanner causes an amplitude of the vibrations of the optical fiber to change over time, and
the correcting of the phase calculates a correction amount for the phase on the basis of the change over time in the amplitude of the vibrations of the optical fiber in addition to the distortion correction amount.

5. The light-scanning endoscope according to claim 2, wherein
the light-scanner causes an amplitude of the vibrations of the optical fiber to change over time, and
the correcting of the phase calculates a correction amount for the phase on the basis of the change over time in the amplitude of the vibrations of the optical fiber in addition to the distortion correction amount.

6. The light-scanning endoscope according to claim 1, further comprising a position sensitive detector configured to detect the light irradiation positions on the imaging subject.

7. The light-scanning endoscope according to claim 6, wherein the controlling of the timing controls the timing at which the light is emitted from the optical fiber so that the light is emitted at equal phase intervals.

8. The light-scanning endoscope according to claim 7, wherein
the light-scanner causes an amplitude of the vibrations of the optical fiber to change over time, and
the correcting of the phase calculates a correction amount for the phase on the basis of the change over time in the amplitude of the vibrations of the optical fiber in addition to the distortion correction amount.

9. The light-scanning endoscope according to claim 6, wherein
the light-scanner causes an amplitude of the vibrations of the optical fiber to change over time, and
the correcting of the phase calculates a correction amount for the phase on the basis of the change over time in the amplitude of the vibrations of the optical fiber in addition to the distortion correction amount.

10. The light-scanning endoscope according to claim 1, wherein the controlling of the timing controls the timing at which the light is emitted from the optical fiber so that the light is emitted at equal phase intervals.

11. The light-scanning endoscope according to claim 10, wherein
the light-scanner causes an amplitude of the vibrations of the optical fiber to change over time, and
the correcting of the phase calculates a correction amount for the phase on the basis of the change over time in the amplitude of the vibrations of the optical fiber in addition to the distortion correction amount.

12. The light-scanning endoscope according to claim 1, wherein the light-scanner causes an amplitude of the vibrations of the optical fiber to change over time, and
the correcting of the phase calculates a correction amount for the phase on the basis of the change over time in the amplitude of the vibrations of the optical fiber in addition to the distortion correction amount.

13. The light-scanning endoscope according to claim 1, wherein the adjusting of the distortion correction amount comprises:
calculating an index value that represents linearity of the row of irradiation positions;
determining whether the index value is equal to or greater than a predetermined threshold;

in response to the index value being equal to or greater than the predetermined threshold, reperforming the adjusting of the distortion correction amount by changing the distortion correction amount; and in response to the index value being less than the predetermined threshold, finishing the adjusting of the distortion correction amount.

14. A light-scanning-endoscope operating method comprising:

emitting, from a vibrating optical fiber, light with the same phase as the vibrations of the optical fiber;

evaluating a linearity of a row of light irradiation positions, on an imaging subject, of the light emitted from the optical fiber;

based on a result of the evaluating, adjusting a distortion correction amount to bring the row closer to a straight line;

based on the adjusted distortion correction amount, correcting the phase at which the light is emitted from the optical fiber; and controlling a timing at which the light is emitted from the optical fiber so that the light is emitted at the corrected phase.

15. The light-scanning-endoscope operating method according to claim 14, wherein the adjusting of the distortion correction amount comprises:

calculating an index value that represents linearity of the row of irradiation positions;

determining whether the index value is equal to or greater than a predetermined threshold;

in response to the index value being equal to or greater than the predetermined threshold, reperforming the adjusting of the distortion correction amount by changing the distortion correction amount; and in response to the index value being less than the predetermined threshold, finishing the adjusting of the distortion correction amount.

16. A correcting apparatus for a light-scanning endoscope, comprising:

a light-scanner that, by vibrating an optical fiber, scans light emitted from the optical fiber; and one or more processors comprising hardware, the one or more processors being configured to:

control a timing at which the light is emitted from the optical fiber so that the light is emitted with the same phase as the vibrations of the optical fiber;

evaluate a linearity of a row of light irradiation positions, on an imaging subject, of the light emitted from the optical fiber;

based on a result of the evaluation, adjust a distortion correction amount to bring the row closer to a straight line; and based on the adjusted distortion correction amount, correct the phase at which the light is emitted.

17. The correcting apparatus according to claim 16, wherein the controlling of the timing controls the timing at which the light is emitted from the optical fiber so that the light is emitted at equal phase intervals.

18. The correcting apparatus according to claim 17, wherein the light-scanner causes an amplitude of the vibrations of the optical fiber to change over time, and the correcting of the phase calculates a correction amount for the phase on the basis of the change over time in the amplitude of the vibrations of the optical fiber in addition to the distortion correction amount.

19. The correcting apparatus according to claim 16, wherein the light-scanner causes an amplitude of the vibrations of the optical fiber to change over time, and the correcting of the phase calculates a correction amount for the phase on the basis of the change over time in the amplitude of the vibrations of the optical fiber in addition to the distortion correction amount.

20. The correcting apparatus according to claim 16, wherein the adjusting of the distortion correction amount comprises:

calculating an index value that represents linearity of the row of irradiation positions;

determining whether the index value is equal to or greater than a predetermined threshold;

in response to the index value being equal to or greater than the predetermined threshold, reperforming the adjusting of the distortion correction amount by changing the distortion correction amount; and in response to the index value being less than the predetermined threshold, finishing the adjusting of the distortion correction amount.

* * * * *